United States Patent
Spatz et al.

(10) Patent No.: US 10,898,619 B2
(45) Date of Patent: Jan. 26, 2021

(54) INTRAOCULAR DEVICE AND METHOD FOR PREPARING THE SAME

(71) Applicant: Max-Planck-Gesellschaft zur Foerderung der Wissenschaften e. V., Munich (DE)

(72) Inventors: Joachim P. Spatz, Stuttgart (DE); Fania Geiger, Leonberg (DE); Michael Thaller, Stuttgart (DE); Christian Lingenfelder, Ulm (DE); Heike Boehm, Weinheim (DE)

(73) Assignee: Max-Planck-Gesellschaft zur Foerderung der Wissenschaften e. V., Munich (DE)

( * ) Notice: Subject to any disclaimer, the term of this patent is extended or adjusted under 35 U.S.C. 154(b) by 480 days.

(21) Appl. No.: 15/741,717

(22) PCT Filed: Jul. 6, 2016

(86) PCT No.: PCT/EP2016/001155
§ 371 (c)(1),
(2) Date: Jan. 3, 2018

(87) PCT Pub. No.: WO2017/005362
PCT Pub. Date: Jan. 12, 2017

(65) Prior Publication Data
US 2018/0193535 A1   Jul. 12, 2018

(30) Foreign Application Priority Data

Jul. 6, 2015   (EP) ................................ 15002024

(51) Int. Cl.
*A61L 31/10*   (2006.01)
*A61F 9/007*   (2006.01)
(Continued)

(52) U.S. Cl.
CPC .......... *A61L 31/10* (2013.01); *A61F 9/00781* (2013.01); *A61L 27/06* (2013.01);
(Continued)

(58) Field of Classification Search
CPC ........ A61L 27/06; A61L 27/34; A61F 9/0072; A61F 9/00781
See application file for complete search history.

(56) References Cited

U.S. PATENT DOCUMENTS 5,002,582 A * 3/1991 Guire .................... A61F 2/0077
427/2.24
5,263,992 A * 11/1993 Guire .................... A61F 2/0077
436/501
(Continued)

FOREIGN PATENT DOCUMENTS

CN   101005812 A   7/2007
CN   101433736 A   5/2009
(Continued)

OTHER PUBLICATIONS

Rezania et al. Bioactivation of metal oxide surfaces 1. Surface characterization and cell response. Langmuir: the ACS journal of surfaces and colloids 15, 6931-6939 (1999) (Year: 1999).*
(Continued)

*Primary Examiner* — Catharine L Anderson
*Assistant Examiner* — Arjuna P Chatrathi
(74) *Attorney, Agent, or Firm* — Caesar Rivise, PC

(57) ABSTRACT

The present invention relates to an ocular device for regulating intraocular fluid pressure comprising or consisting of a tubular body wherein the inner surface of the tubular body or the inner and outer surface is/are coated with covalently immobilized hyaluronic acid (HA). In more specific embodiments, the tubular body comprises or consists of a biocompatible material selected from the group comprising
(Continued)

a biocompatible metal such as titanium, ceramics, glass, polymers and composites thereof, and the immobilized hyaluronic acid molecules are linked with further HA molecules to form a HA hydrogel. The ocular device is a stent free from mechanical valves or other mechanical means for actively regulating the flow of intraocular fluid.

15 Claims, 8 Drawing Sheets

(51) Int. Cl.
| | |
|---|---|
| C08B 37/08 | (2006.01) |
| C08J 3/075 | (2006.01) |
| C08J 3/24 | (2006.01) |
| C09D 105/08 | (2006.01) |
| C08L 5/08 | (2006.01) |
| A61L 27/34 | (2006.01) |
| A61L 27/20 | (2006.01) |
| A61L 27/06 | (2006.01) |
| A61L 31/02 | (2006.01) |
| A61L 31/04 | (2006.01) |
| A61L 31/14 | (2006.01) |

(52) U.S. Cl.
CPC .............. *A61L 27/20* (2013.01); *A61L 27/34* (2013.01); *A61L 31/022* (2013.01); *A61L 31/026* (2013.01); *A61L 31/04* (2013.01); *A61L 31/145* (2013.01); *C08B 37/0072* (2013.01); *C08J 3/075* (2013.01); *C08J 3/24* (2013.01); *C08L 5/08* (2013.01); *C09D 105/08* (2013.01); *A61F 2240/001* (2013.01); *A61L 2430/16* (2013.01); *C08J 2305/08* (2013.01)

(56) References Cited

U.S. PATENT DOCUMENTS

| | | | | |
|---|---|---|---|---|
| 6,129,956 | A * | 10/2000 | Morra | A61L 29/085 427/535 |
| 6,186,974 | B1 * | 2/2001 | Allan | A61F 9/00781 604/30 |
| 6,585,765 | B1 * | 7/2003 | Hossainy | A61L 27/34 427/2.24 |
| 8,313,523 | B2 | 11/2012 | Banas et al. | |
| 8,672,870 | B2 * | 3/2014 | Silvestrini | A61F 9/00781 604/294 |
| 9,644,076 | B2 | 5/2017 | Boehm et al. | |
| 2003/0212383 | A1 * | 11/2003 | Cote | A61F 9/00781 604/523 |
| 2005/0084514 | A1 * | 4/2005 | Shebuski | A61K 31/4433 424/426 |
| 2005/0119737 | A1 * | 6/2005 | Bene | A61F 9/00781 623/4.1 |
| 2006/0147492 | A1 | 7/2006 | Hunter et al. | |
| 2007/0276472 | A1 | 11/2007 | Gazza | |
| 2009/0130293 | A1 | 5/2009 | Shykind et al. | |
| 2014/0343476 | A1 * | 11/2014 | Penhasi | A61F 9/00781 604/8 |

FOREIGN PATENT DOCUMENTS

| | | |
|---|---|---|
| CN | 103357072 A | 10/2013 |
| CN | 103613686 A | 3/2014 |
| EP | 0552593 A1 | 7/1993 |
| WO | 0150943 A2 | 7/2001 |
| WO | 2004087234 A1 | 10/2004 |
| WO | 2012037330 A1 | 3/2012 |
| WO | 2014048564 A1 | 4/2014 |
| WO | 2016094533 A1 | 6/2016 |

OTHER PUBLICATIONS

Shu et al. Disulfide cross-linked hyaluronan hydrogels. Biomacromolecules 3, 1304-1311 (2002) (Year: 2002).*
Mukherjee et al. Regioselective ring opening of epoxides with thiols in water. Archive for Organic Chemistry 11, 46-55 (2008) (Year: 2008).*
English-language abstract of CN103357072 (2013).
English-language abstract of CN103613686 (2014).
Office Action dated Mar. 26, 2020 for European Application No. 15002024.6.
Hersel et al. (2003). RGD modified polymers: biomaterials for stimulated cell adhesion and beyond. Biomaterials, 24 (24), 4385-4415.
Shu et al. (2002). Disulfide cross-linked hyaluronan hydrogels. Biomacromolecules, 3(6), 1304-1311.
Thaller et al. (2017). Hyaluronsäuregele zur Druckregulierung in der Glaukomtherapie. Der Ophthalmologe, 1-7.
English language abstract for Thaller et al. (2017). Hyaluronsäuregele zur Druckregulierung in der Glaukomtherapie. Der Ophthalmologe, 1-7.
European Search Report from corresponding EP 15002024 dated Jan. 20, 2016.
International Search Report from corresponding PCT/EP2016/001155 dated Oct. 10, 2016.
Thaller et al. (2016). Hyaluronan hydrogel modified intraocular implants for glaucoma treatment. Dissertation. Fakultät for Chemie and Geowissenschaften. Institute of Physical Chemistry. p. 1-145.

* cited by examiner

INTRAOCULAR DEVICE AND METHOD FOR PREPARING THE SAME

CROSS-REFERENCE TO RELATED APPLICATIONS

This application is a U.S. National Phase Application of PCT/EP2016/001155, filed Jul. 6, 2016, which claims priority to EP 15002024.6 filed Jul. 6, 2015, the contents of which applications are incorporated herein by reference in their entireties for all purposes.

BACKGROUND OF THE INVENTION

Glaucoma is a widespread disease which in its late stages results in blindness. In Germany alone each year 10,000 patients turn blind due to the concomitant damage of the optical nerve. The number of Glaucoma patients is growing every year and due to the fact that people become older these days a long-term treatment is very desirable.

Any Glaucoma treatment aims to reduce the increased eye pressure of Glaucoma patients to a normal level. Mild forms of Glaucoma can be treated pharmaceutically. However, all pharmaceutical treatments are paired with side effects.

Until today, unlike in other fields of surgery, no gold standard could be established. This is mainly due to the fact that the known surgical options are neither completely reliable nor long lasting. All methods of the prior art are rather costly and burdensome for the patient.

For example, if stents are implanted, the main contra-indications are stenosis of the inner lumen or displacement of the stent. In late stage Glaucoma a surgical procedure is the only option to preserve eye sight. Since each patient has a different eye pressure, a device which ideally regulates the eye pressure based on the existing pressure is required. In order to prevent stenosis and therefore the need for expensive and stressing exchange of the implant, the interior of the stent has to repel cells. On the other hand, a fast incorporation into the tissue without promoting inflammation is desired, i.e. a cell attracting surface on the outside of the stent. Inflammation around the stent could possibly lead to scar tissue and would hinder the absorption of aqueous humor flowing through the stent.

A number of stents for the treatment of Glaucoma are already available and described in the literature (see, e.g. WO 01/50943 A2, U.S. Pat. No. 8,672,870 B2, US 2006/0147492, US 2014/0343476 A1).

However, these stents of the prior art are either not able to reach all the main objects of a high performance ocular stent or shunt, i.e. draining a specific amount of aqueous humor, preventing the stent from stenosis, a good incorporation into the tissue and a long lifespan, or have a rather complex composition and design which renders their production costly and also renders the product more prone to defects (in particular in the course of a long lifespan).

Therefore, there is still a demand for an improved ocular shunt or stent which is able to overcome or at least alleviate these drawbacks of the prior art.

The above mentioned objects are achieved according to the present invention by providing the ocular device according to claim 1 and the method of preparation according to claim 15. More specific or preferred embodiments of the invention are the subject of further claims.

DESCRIPTION OF THE INVENTION

According to the invention, an ocular device for regulating intraocular fluid pressure comprises or consists of a tubular body wherein at least the inner surface of the tubular body is partially or completely coated with covalently immobilized hyaluronic acid.

In one specific embodiment, only the inner surface of the tubular body is partially or completely, preferably completely, coated with the covalently immobilized hyaluronic acid or a corresponding hyaluronic acid based hydrogel, whereas in another specific embodiment, both the inner and outer surface of the tubular body are partially or completely coated with covalently immobilized hyaluronic acid or a corresponding hyaluronic acid based hydrogel.

The material of the tubular body is not especially limited as far as it is a biocompatible material and suitable materials are known in the art.

More specifically, the tubular body consists of a biocompatible material selected from the group comprising a biocompatible metal such as titanium and titanium alloys, stainless steel, platinum, gold, tantalum, chrome cobalt alloys, ceramics, glass, polymers such as poly(alkyl) acrylates, polycarbonates, and composites thereof.

Typically, the tubular body has a length in the range from 2.5 mm to 0.3 mm or 2.5 mm to 0.5 mm, preferably from 1.5 mm to 0.4 mm, 0.5 mm or 0.8 mm, in particular in the range from 0.3 mm to 0.5 mm or 0.6 mm, and a diameter in the range from 2 mm to 100 µm, preferably from 1 mm to 200 µm, and a lumen with an inner diameter in the range from 1 mm to 50 µm, preferably from 600 µm to 100 µm, such as 100 µm to 300 µm or 150 µm to 250 µm.

The tubular body and/or the lumen may have any suitable cross-section, e.g. a round, rectangular, circular or annular cross-section. The tubular body may be essentially linear or curved, preferably linear, and its diameter and/or the diameter of its lumen may be constant or variable. For example, the tubular body may have at least one tapered end portion.

In one preferred embodiment as, the tubular body has (slightly) concave dimensions in the longitudinal direction (as exemplarily illustrated in FIG. 12 on the left) and, preferably, a length in the range from 300 µm to 500 µm or 600 µm and a smallest internal diameter typically in the range from 100 µl to 300 µm or 400 µm, more specifically in the range from 150 µm to 250 µm. This shape supports positioning of the stent in tissues.

In a specific embodiment, the tubular body and/or the lumen thereof has an annular cross-section.

Optionally, the tubular body (with or without a tapered end) may be attached to at least one holding or retaining ring (as exemplarily illustrated in FIG. 12 on the right). In this case, the shape of the stent may be similar to that of a top hat and the diameter of the retaining ring may be in the range from 300-600 µm or 300-500 µm, preferably 350-450 µm, the total length of the stent preferably is in the range from 300 µm to 500 µm and the internal diameter of the tubular body preferably is in the range from 100 µl to 300 µm or 400 µm, more specifically in the range from 150 µm to 250 µm.

The terms "ocular device" or "intraocular device" as used herein principally encompass any device capable of regulating the intraocular fluid pressure by providing a controlled flow of intraocular fluid through said device. In particular, the ocular device may be a device such as a "stent" which regulates the aqueous flow and therewith the eye pressure passively by providing a conduit having a predetermined drainage and flow capacity, or a "shunt" which comprises additional mechanical means for actively regulating and varying the flow such as valves etc. Preferably, the ocular device of the invention is a stent.

In a preferred embodiment of the invention, the ocular device (in particular stent) is a one-part device consisting only of said tubular body coated with immobilized hyaluronic acid or a HA gel.

The simple geometry of the device according to the present invention allows i.a. its implantation through the pars plana into the posterior chamber or into the choroid; contrary to this, the stent disclosed in US 2014/034376 A1 is implanted in the chamber angle. Other suitable implantation sites could be a position in the vicinity of the "Schlemm-Kanal" or a position in the sclera.

The intraocular fluid may be drained, e.g. into the veins, the connective tissue, the adipose tissue surrounding the eye, or another vascularized area in the vicinity of the eye.

Typically, the surface of the tubular body is or has been functionalized according to methods principally known in the art with reactive groups capable to react with corresponding functional groups of the hyaluronic acid and therefore the hyaluronic acid is immobilized via a covalent bond resulting from a covalent reaction between said functional groups.

Covalent attachment of the HA to the surface will prevent the HA or HA hydrogel from being pushed out of the tubular body, e.g. by the eye pressure.

The reactive groups on the surface of the tubular body may be for example epoxide groups, amine groups, maleimides, acrylic groups, azides etc.

Methods for introducing functional groups into hyaluronic acid are also known in the art (e.g. Shu et al., *Biomacromolecules* 3, 1303-1311 (2002)).

More specifically, the ocular device of the invention comprises or consists of a tubular body made of titanium wherein at least the inner surface, preferably the outer and inner surface, of the tubular body has been silanized and thiol-modified hyaluronic acid molecules are immobilized onto said surfaces via a covalent bond which is the result of a coupling reaction between epoxide groups on the silanized titanium surface and hydroxyl- and/or thiol groups of thiol-modified hyaluronic acid.

Typically, the respective surface of the device is activated prior to the introduction of the reactive groups. This may be effected, e.g., with an alkaline solution (such as Extran® MA01), plasma or $H_2SO_4/H_2O_2$.

For the silanization treatment any known silanizing agent, e.g. (3-glycidyloxypropyl)trimethoxysilane, may be used.

In a typical embodiment, the immobilized hyaluronic acid molecules are linked with further HA molecules to form a HA hydrogel. Suitable crosslinkers are well known in the art, e.g. from WO 002014048564.

Specifically, the immobilized hyaluronic acid molecules are linked with further HA molecules to form a HA hydrogel via crosslinkers with acrylic groups selected from the group comprising polyethylene(glycol)-diacrylamide (PEG-DA), N,N'-methylenebisacrylamide (MBAA), $N^3,N^5$-bis(2-acrylamidoethyl) pyridine-3,5-dicarboxamide, 3,5-((2-acrylamidoethyl)carbamoyl)-1-methylpyridin-1-ium iodide, piperazine diacrylamide, N,N'-(1,2-dihydroxyethylene) bisacrylamide, N,N-bis(acryloyl) cystamine.

The coupling of the modified HA molecules to the reactive groups on the tubular body and the optional crosslinking steps can be performed sequentially or simultaneously.

Gel properties can be fine-tuned by the choice of the crosslinker, crosslinker concentration and degree of HA thiolation and optionally other/further HA modifications. This enables, i.a., to achieve a controlled flow of aqueous or intraocular fluid, respectively, through the ocular device in order to adjust for different eye pressures and to achieve a desired target eye pressure.

Typically, the crosslinkers will also stabilize the HA hydrogel against degradation, hyaluronidase digestion and prevent cell attachment in the tube inside; this will lead to an enhanced life time of the implant.

In one embodiment, the immobilized hyaluronic acid molecules or the HA hydrogel on the outside of the ocular device is/are linked with additional cell adhesion-regulating molecules, such as cyclic RGD peptides or other cell adhesion-regulating molecules known in the art.

This can be achieved by, e.g., integrating the cRGD in the HA gel at the outside of the ocular device (such as a stent or shunt) by adding cyclic RGD with an appropriate crosslinker and ratio to the HA polymerization reaction (Hersel et al. (2003), Biomaterials 24, 4385-4415).

However, a major advantage of the ocular device of the present invention resides in the fact that the hyaluronic acid or HA hydrogel is able to fulfil several important functions and acts simultaneously as a cell adhesion regulating agent and as an eye pressure regulating agent as well.

In particular, the HA or HA hydrogel inside the ocular device will regulate the eye pressure of Glaucoma patients by draining aqueous humor e.g. into the "Schlemm-Kanal". As already mentioned above, the HA gel can be modified through several parameters and adjusted for different eye pressures. This is not only to prevent pressure form building up and create dangerous peaks but also to control a minimal pressure in order to allow hypotonic patients to be treated or prevent hypotony after surgery. The crosslinkers used for the production of the HA gel can advantageously selected to equip the gel either with cell repellent properties—preventing also lens epithelia cell growth and therefor stent blocking—(inside) or with cell attracting properties (outside) as desired.

Therefore, the surface of the tubular body may be—and in one preferred embodiment is—free from other cell adhesion-regulating molecules than those of hyaluronic acid or the HA hydrogel and is still able to show the desired cell adhesion regulating properties.

The basic principle for the creation of a new type of glaucoma implant is illustrated in FIG. 6. The basic design is a tube (preferably a titanium tube) (a), capable of draining fluid from the glaucomatous eye in order to reduce the intraocular pressure. Hydrogels made from hyaluronan are selectively grafted on the outer surface (b) and/or into the interior (c) of the tube. These modifications should on the one hand enable an improved cell proliferation to increase the biocompatibility of the tube (d) while preventing a blockade of the interior through cell proliferation (e). The hydrogel on the interior further acts as a valve and control the amount of liquid drained from the eye for a regulated decrease of intraocular pressure (f).

A further aspect of the present invention relates to a method for preparing the ocular device described above which comprises at least the following steps:

a) providing a tubular body having predetermined dimensions;

b) introducing functional groups onto the inner surface or both the inner surface and outer surface of the tubular body;

c) reacting the functional groups of the inner surface or of the inner and outer surface of the tubular body with reactive groups of hyaluronic acid resulting in covalently immobilized hyaluronic acid molecules;

d) optionally crosslinking of the immobilized hyaluronic acid molecules with further HA molecules and suitable crosslinkers to form a HA hydrogel.

More specifically, the tubular body provided in step a) is made of titanium, the functional groups introduced in step b) are epoxide groups introduced by silanization of the titanium surface, and the immobilization of hyaluronic acid in step c) occurs via a coupling reaction of epoxide groups on the silanized titanium surface and hydroxyl and/or thiol groups of thiol-modified hyaluronic acid.

Another aspect of the invention relates to a method and device wherein the inside or lumen of a stent is essentially completely filled with a hyaluronic acid (HA) hydrogel regulating the eye pressure and preventing clogging of the stent with cells (stenosis). The HA hydrogel is immobilized on the inner stent surface and crosslinked with a crosslinker except for a "defect" or channel pervading the gel horizontally in the middle of the tube. In the swollen gel state, the defect cannot be seen, the gel occupies the inside of the stent completely. Due to an elevated eye pressure the gel will be compressed at the "defect" resulting in a channel allowing eye fluid to be trained (FIG. 7). The elastic counterforce of the gel is acting against the liquid pressure closing the channel when the pressure has dropped to a certain value. The pressure of opening and closing of the channel can be regulated by the dimensions of the stent and the gel properties such as HA concentration, thiolation degree of HA, type of crosslinker, and crosslinker concentration as well as the size of the defect.

The gel "defect" or channel can be generated either mechanically or optically (as shown in FIG. 8). Mechanically: to prevent the gel from crosslinking in the middle of the channel while the gel is being formed, a thin elongated element, such as a thread or a fiber, in particular a glass fiber, is introduced leaving a small channel behind after gel formation. This channel will be closed after gel swelling preventing water flow till the desired pressure is reached. Optically: the channel can also be "burned" into the gel after gel formation but before swelling using a laser. The resulting channel will also disappear after swelling and open up at a certain pressure as described above.

Thus, one method for preparing an ocular device of the invention exhibiting such a channel comprises at least the following steps:

a) providing a tubular body having predetermined dimensions and providing an elongated removable element, such as a thread or a fiber, in the lumen of the tubular body in a predetermined distance, preferably equidistant, from the inner surfaces of the tubular body, and which element extends in the longitudinal direction of the lumen of the tubular body;

b) introducing functional groups onto the inner surface or the outer and inner surface of the tubular body;

c) reacting the functional groups of the inner surface or of the inner and outer surface of the tubular body with reactive groups of hyaluronic acid resulting in covalently immobilized hyaluronic acid molecules;

d) crosslinking the immobilized hyaluronic acid molecules on at least the inner surface with further HA molecules and suitable crosslinkers to form a crosslinked HA hydrogel;

e) removing the elongated removable element after gel formation leaving a channel with dimensions corresponding to that of said elongated element in the crosslinked hydrogel.

Another method for preparing an ocular device of the invention exhibiting such a channel comprises at least the following steps:

a) providing a tubular body having predetermined dimensions;

b) introducing functional groups onto the inner surface or the outer and inner surface of the tubular body;

c) reacting the functional groups of the inner surface or of the inner and outer surface of the tubular body with reactive groups of hyaluronic acid resulting in covalently immobilized hyaluronic acid molecules;

d) crosslinking the immobilized hyaluronic acid molecules on at least the inner surface with further HA molecules and suitable crosslinkers to form a crosslinked HA hydrogel which fills the lumen of the tubular body;

e) generating a (small) channel in the crosslinked HA hydrogel which extends in the longitudinal direction of the tubular body by irradiating an open end portion of the crosslinked HA hydrogel obtained after step d) above in the lumen of the tubular body with a laser beam in the longitudinal direction of the tubular body and the crosslinked HA hydrogel with a sufficient energy and for a sufficient time period to obtain an end-to-end channel in said crosslinked HA hydrogel.

EXAMPLE 1

Figure 1:
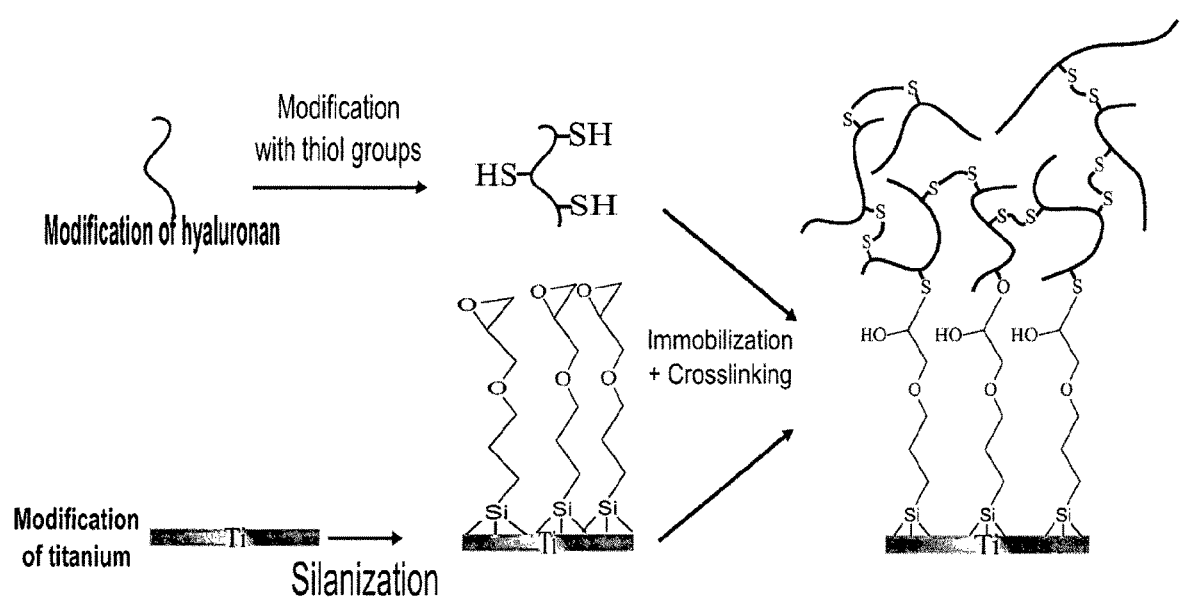
FIG. 1: Schematic drawing of the immobilization and crosslinking of HA on a silanized titanium surface

Preparation of a HA Coated Ocular Device

Modification of Hyaluronan with Thiol Groups

The following protocol is an adapted and modified version of the protocol published by the group of Prestwich (Shu et al. in *Biomacromolecules* 3, 1303-1311 (2002)).

1 g (2.5 mmol) hyaluronic acid (HA; $M_n$=60 kDA) was dissolved in 100 ml MilliQ water (concentration=10 mg/ml) and the pH was adjusted to 4.75. 1.33 g 3,3'-dithiobis (propanoic hydrazide (DTPH) were added and after complete dissolution, the reaction was initiated by the addition of 960 mg (5 mmol) N-(3-dimethylaminopropyl)-N'-ethyl-carbodiimide hydrochloride (EDC), commenced for variable times (10 min to 2 h depending on the desired thiolation grade) at room temperature while the pH was manually kept at 4.75. Raising the pH to 7.5 stopped the reaction. The mixture was 02-purged with Argon (30 min) and 5 g DTT (dithiothreitol) were added before adjusting the pH to 8.5 followed by stirring for 24 h at room temperature. The pH was lowered to 3.5 and the solution dialyzed against diluted HCl (pH=3.5). The purified product solution was frozen and lyophilized yielding the thiolated hyaluronan (HS-HA).

Activation and Silanization of Glass or Titanium Stents

Glass or titanium tubes were immersed in Extran®MA 01 for >2 h. After rinsing in distilled water and drying in an $N_2$ stream, the samples were immediately afterwards incubated (bubble free) in a 2% (v/v) solution of (3-glycidyloxypropyl) trimethoxysilane in toluene (>99.5%) for 24 h. The stents were sonicated in toluene and afterwards EtOH for 15 min each and finally used for the binding of HA.

HA-Gel Formation and Immobilization

Hyaluronan hydrogels were synthesized by mixing a HS-HA solution with a crosslinker (CL) solution. HS-HA and the CL were dissolved separately in a solution of TRIS in balanced salt solution (BSS) (0.4 M, pH=8.5), which was $O_2$ purged using Argon gas before use. The HA and the CL solutions were mixed in a ratio of V(HA solution)/V(CL solution)=7:3. The final concentration of HS-HA varied from 5 mg/ml to 15 mg/ml and the ratio of acrylamide groups to active thiols from 0.2-0.8. The gels were formed under oxygen exclusion at different temperatures depending on the used crosslinker. Exemplary crosslinkers used were NENA ($N^3,N^5$-bis(2-acrylamidoethyl) pyridine-3,5-dicarboxamide), MBAA (N,N'-methylen-bisacrylamide), PEG-DA (polyethylen(glycol) diacrylamide).

To modify only the inside of the stent, several stents were connected with each other using short tubing (length=1-2 cm) and the HA/CL mixture was injected using a syringe. The entrances of the channel were sealed with Parafilm, the whole setup placed into a plastic petri dish, which was flooded with argon and sealed with Parafilm. After polymerization, the tubing was removed and the samples placed in BSS for several days to equilibrate.

For a selective modification of the outer surface, the entrances of the stents were sealed with dentist glue and incubated in a HA/CL solution with 02 exclusion. After polymerization the glue was removed and the samples placed in BSS for several days to equilibrate.

A slightly different approach for preparing the stents of the invention involves starting with a long titanium tube which is filled with the HA-Gel and cut it into small pieces afterwards. This simplifies and fastens the procedure considerably.

Characterization and Tests

Figure 2:
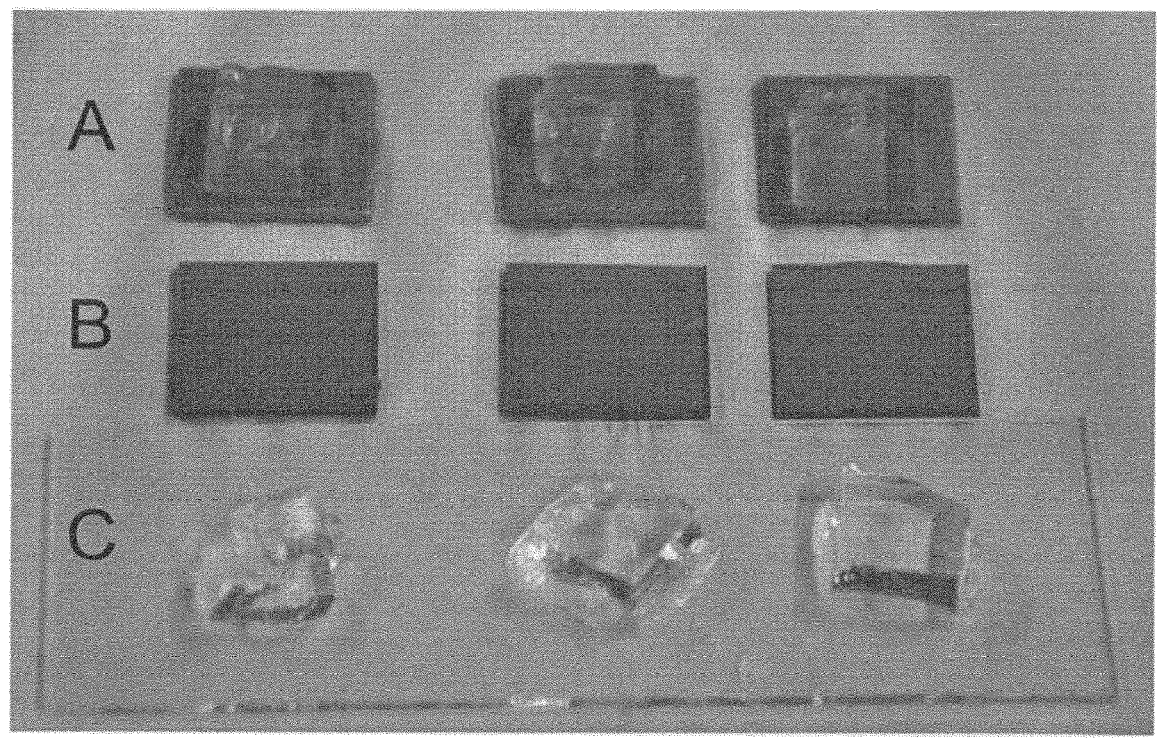
FIG. 2: HA gels produced from thiolated HA and BIS crosslinker on A) silanized and B) non-silanized titanium surfaces; Row C shows the HA gels slipped off the non-silanized surface of B.

FIG. 2 shows HA gels produced from thiolated HA and BIS crosslinker on A) silanized and B) non-silanized titanium surfaces; Row C shows the HA gels which slipped off the non-silanized surface of B.

Figure 3:
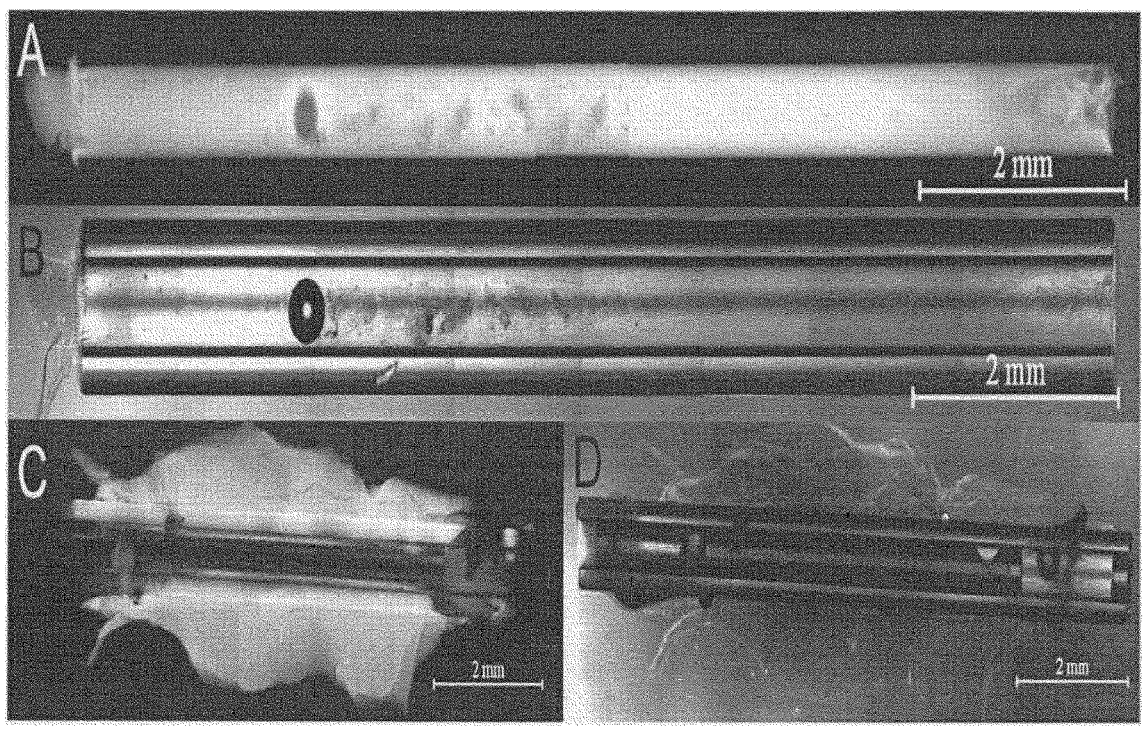
FIG. 3: Glass model stent with a fluorescently labelled HA gel in the inside (A+B) or on the outside (C+D) thereof
Figure 4:
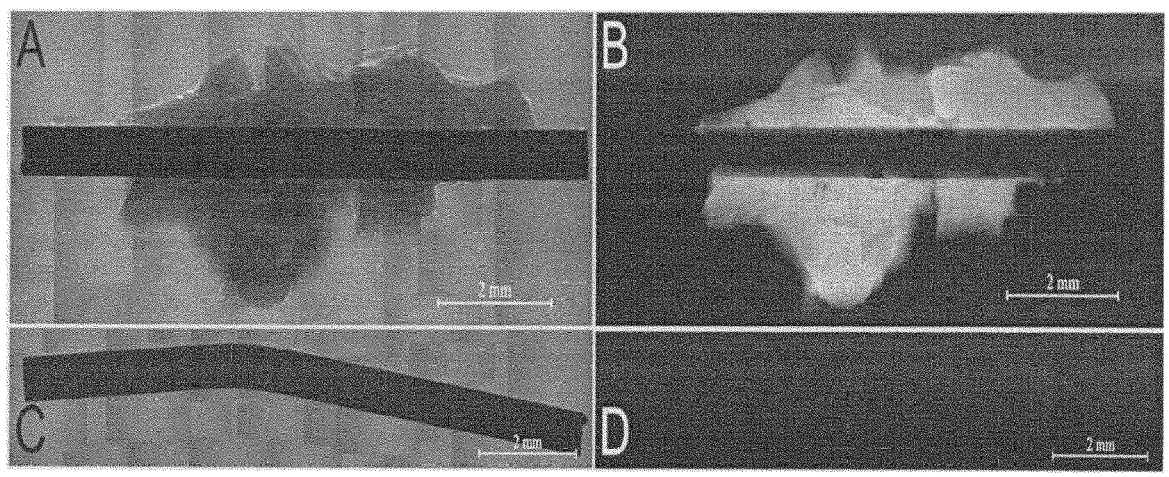
FIG. 4: Titanium stent with a fluorescently labelled HA gel on the outside. A+B: silanized titanium stent; C+D: non-silanized titanium stent
Figure 5:
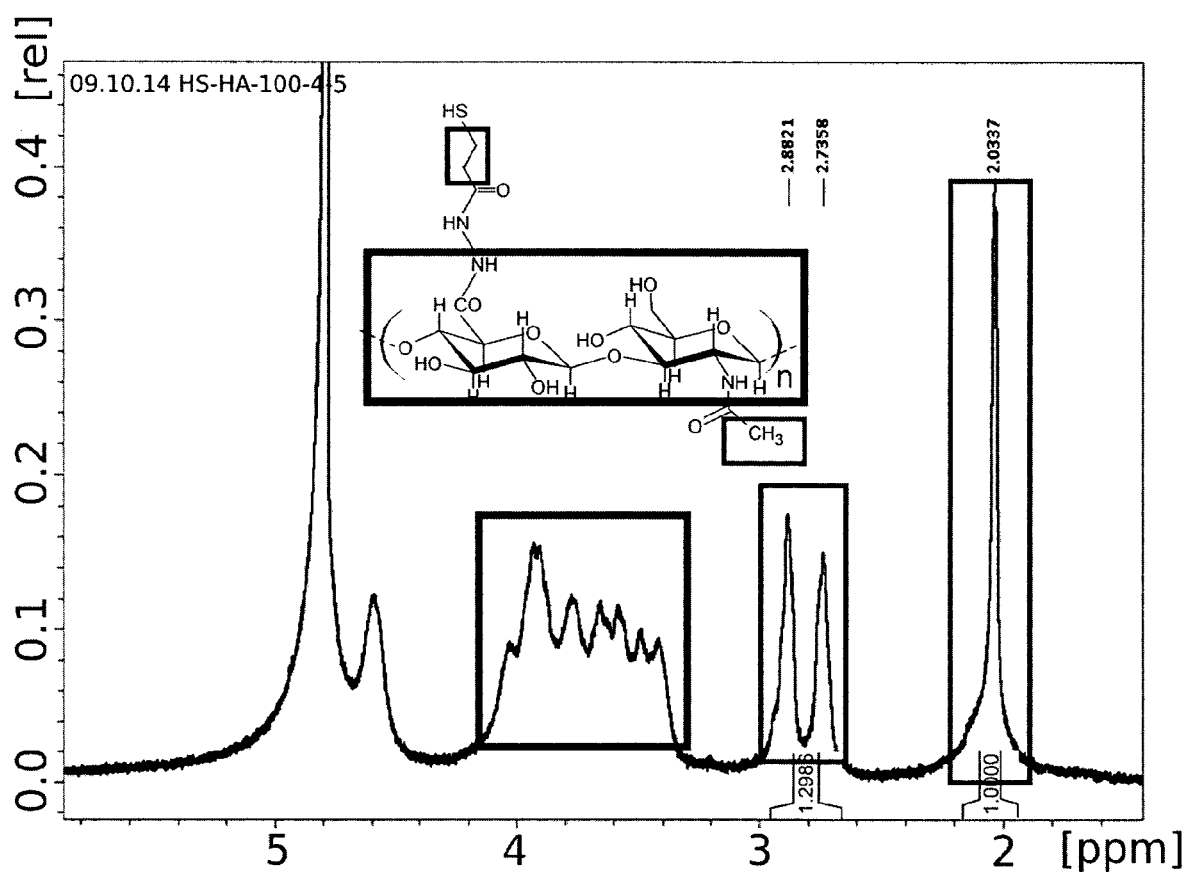
FIG. 5: NMR-spectrum of thiolated hyaluronic acid. The peaks in the middle box represent the introduced thiol-groups.
Figure 6:
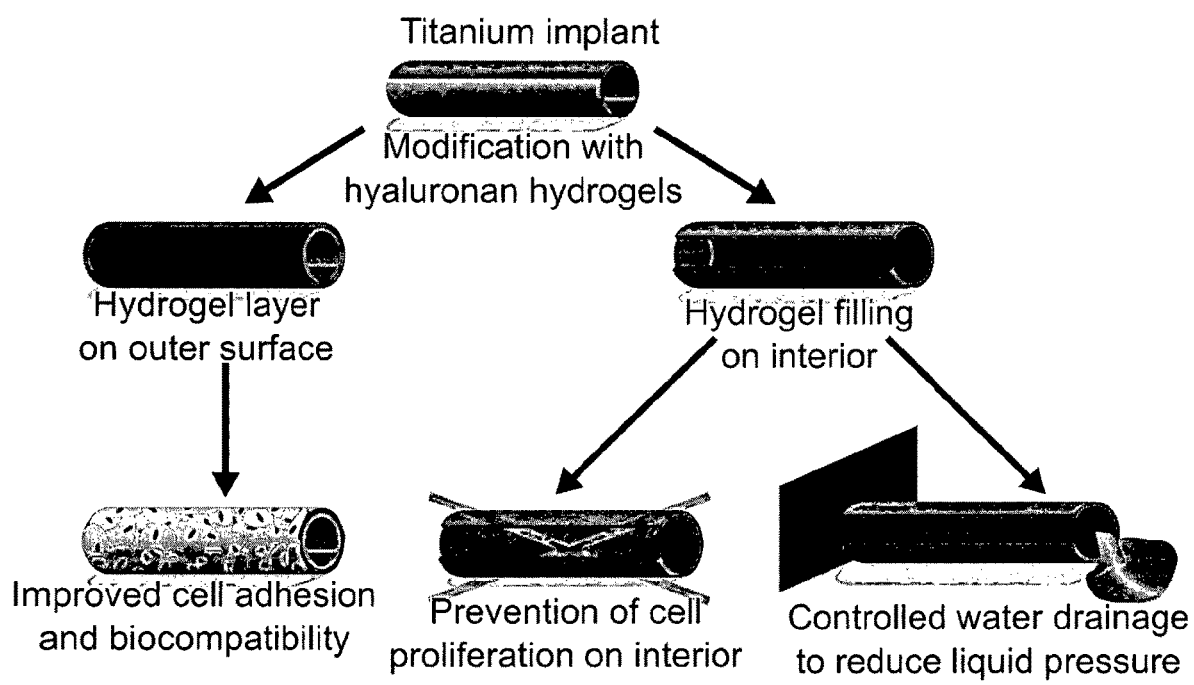
FIG. 6: Basic principle for the creation of a new type of glaucoma implant according to the invention

FIG. 3 shows a glass model stent with a fluorescently labelled HA gel in the inside (A+B) or in the outside (C+D) thereof. Glass can be silanized with the same chemistry as titanium. As mentioned above, a fluorescently labelled and thiolated HA was used to test and visualize the immobilization and crosslinking of a HA gel in the glass model stent. A+C: fluorescent image; B+D: phase contrast FIG. 4 shows a titanium stent with a fluorescently labelled HA gel on the outside. A+B: silanized titanium stent; C+D: non-silanized titanium stent; A+C: phase contrast; B+D: fluorescent image FIG. 5 shows the NMR-spectrum of thiolated hyaluronic acid.

The peaks in the middle box represent the introduced thiol-groups. 3-5 mg of the thiolated HA were dissolved in $D_2O$ and spectra recorded at 300 MHz.

EXAMPLE 2

Preparation of a Stent Filled with a Discontinuous HA Hydrogel

In this embodiment, the inside or lumen of a stent is essentially completely filled with a hyaluronic acid (HA) hydrogel regulating the eye pressure and preventing clogging of the stent with cells (stenosis). The HA hydrogel is immobilized on the inner stent surface and crosslinked with a crosslinker except for a "defect" pervading the gel horizontally in the middle of the tube. In the swollen gel state, the defect cannot be seen and the gel occupies the inside of the stent completely. Due to an elevated eye pressure the gel will be compressed at the "defect" resulting in a channel allowing eye fluid to be trained). The elastic counterforce of the gel is acting against the liquid pressure closing the channel when the pressure has dropped to a certain value. The pressure of opening and closing of the channel can be regulated by the dimensions of the stent and the gel properties such as HA concentration, thiolation degree of HA, type of crosslinker, and crosslinker concentration as well as the size of the defect.

Figure 7:
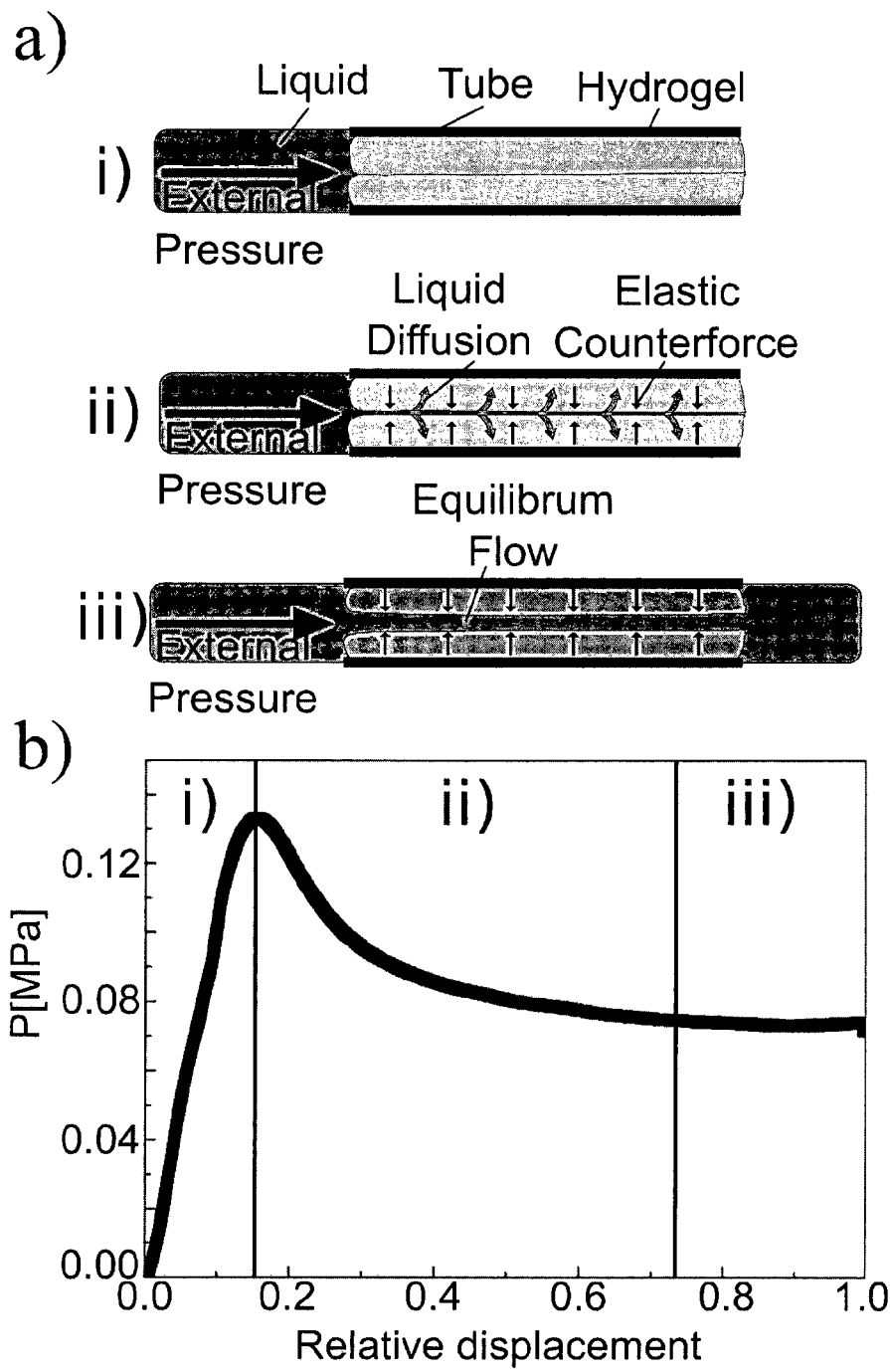
FIG. 7: Putative mechanism (a) and correlation with CPA measurements (b) for pressure-induced liquid flow through HA hydrogel-filled tubes.

FIG. 7 shows the putative mechanism (a) and correlation with CPA measurements (b) for pressure-induced liquid flow through hydrogel-filled tubes. A "flaw" in the form of a small channel is located within the hydrogels. i) As long as the external pressure is below a certain threshold, the channel is "closed" due to a combination of elastic forces of and hydrophilic interactions between the interfaces of hydrogels. No water flow is established. ii) When the pressure is more than that threshold, water infiltrates the system, overcoming the hydrophilic forces and enacting compressive forces upon the hydrogels, which causes the channel to "open". iii) These compressive forces of the external pressure and the elastic counterforces are in balance, which establishes a constant channel size and enables liquid flow.

Figure 8:
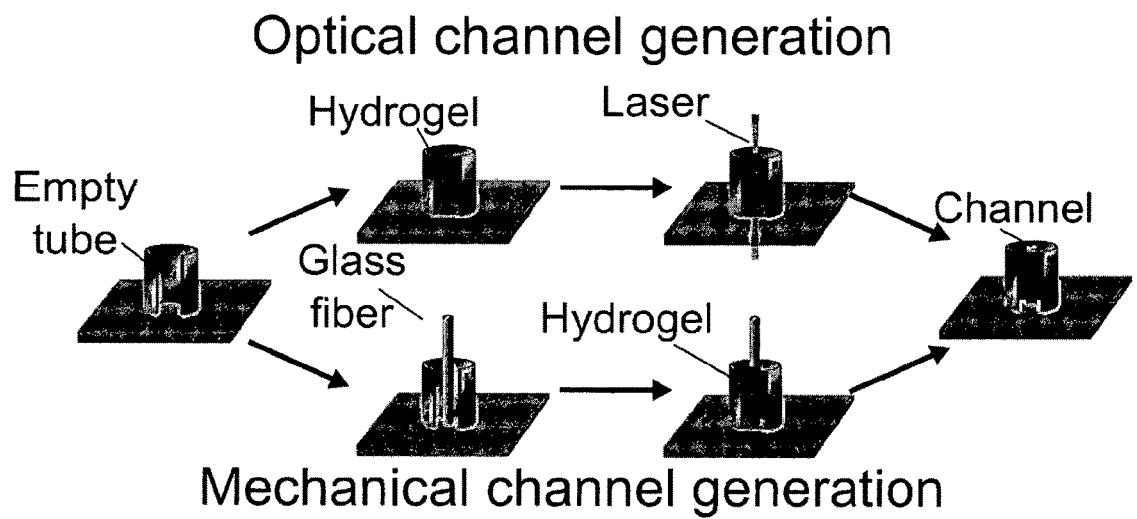
FIG. 8: Alternative approaches for physically creating channels within hydrogel-filled tubes for artificially inducing the ability for liquid pressure regulation. (a): In the optical method covalently immobilized hydrogels were first prepared within tubes and a laser applied to "burn" the channel into the gel. (b): In the mechanical method a small fiber into was placed coaxially into the empty tube. After the gel formation the fiber was removed leaving behind the channel.

The gel "defect" can be generated either mechanically or optically. FIG. 8 illustrates 2 alternative approaches for physically creating channels within hydrogel-filled tubes for artificially inducing the ability for liquid pressure regulation. (a): In the optical method covalently immobilized hydrogels were first prepared within tubes and a laser applied to "burn" the channel into the gel. (b): In the mechanical method a small fiber into was placed coaxially into the empty tube. After the gel formation the fiber was removed leaving behind the channel.

Both approaches were actually used and are described in the doctoral thesis of Michael Thaller (published in March 2016, Rupprecht-Karls Universitat Heidelberg).

Figure 9:
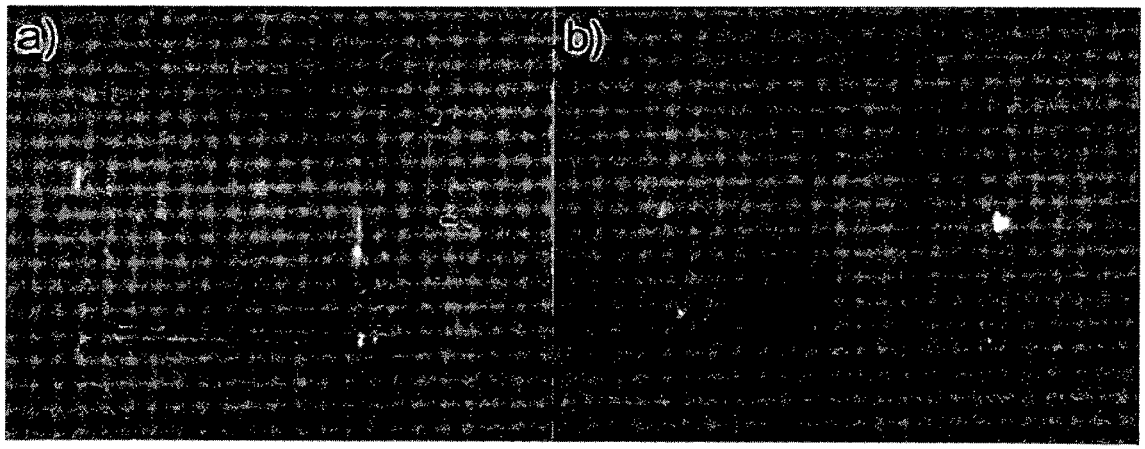
FIG. 9: Hydrogel-filled tube (L=10 mm; ID=5 mm) with a channel created by the mechanical method directly after sample preparation was finished (a) and after 48 hours of incubation in BSS (b).

FIG. 9 shows a hydrogel-filled tube (L=10 mm; ID=5 mm; Mn(HA)=100 kDa; β(HA)=15 mg/mL; TG=0.57; gels synthesized in TRIS/BSS (c(TRIS)=0.4 mol/l; pH=8.5)) with a channel created by the mechanical method directly after sample preparation was finished (a) and after 48 hours of incubation in BSS (b). There was no visual indication of the presence of the channel after the swelling in BSS (Crosslinker: MBAA).

Figure 10:
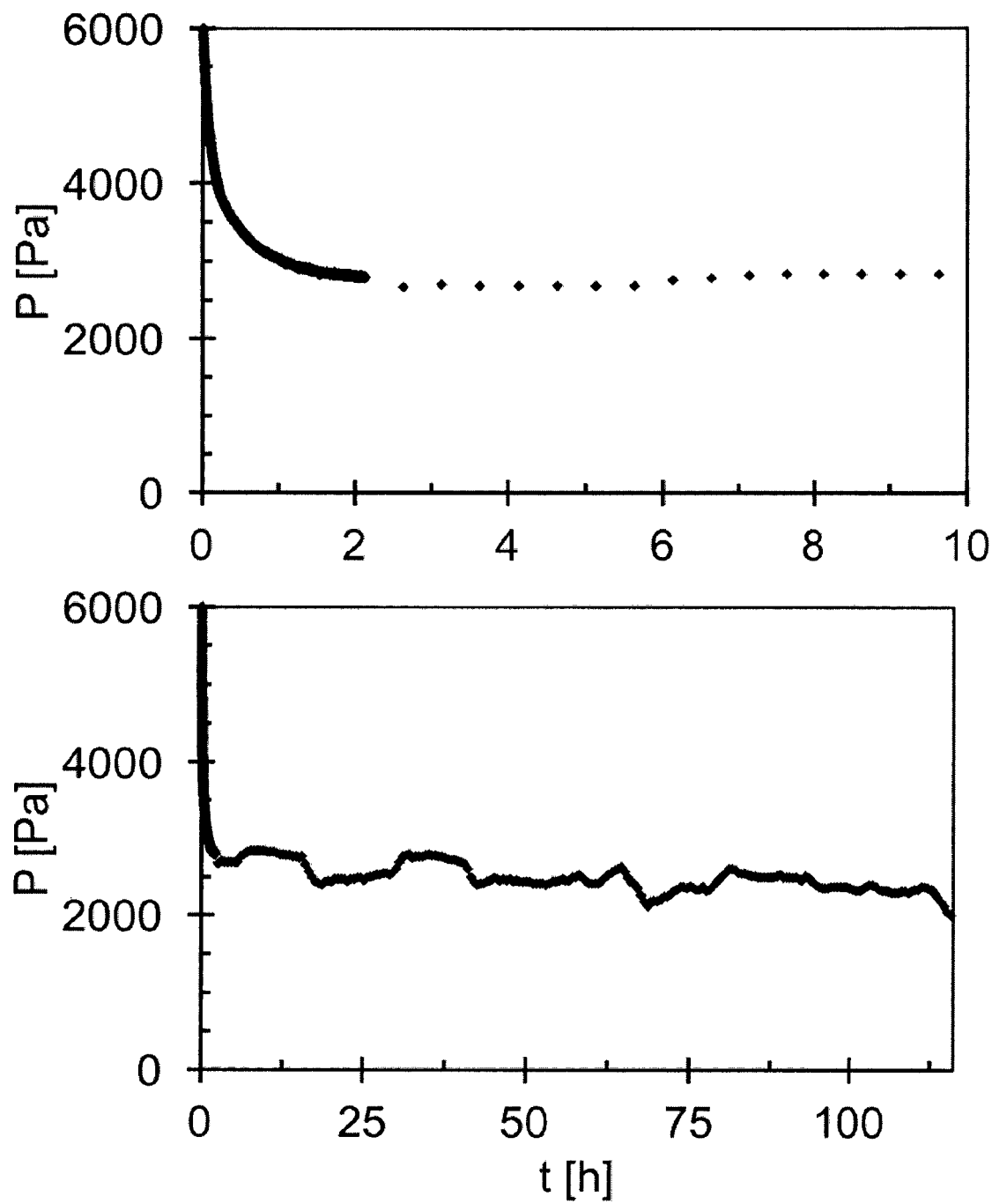
FIG. 10: HPA measurement of a hydrogel-filled tube (ID=5 mm) with channels formed using small glass fibers (diameter=0.1 mm).

FIG. 10 shows the HPA measurement of a hydrogel-filled tube (ID=5 mm) with channels formed using the small glass fibers (diameter=0.1 mm). The pressure dropped to an average level of 2500+/−200 Pa after 2 hours (a) with long-term variations (b) mostly originating from pressure fluctuations within the lab.

Figure 11:
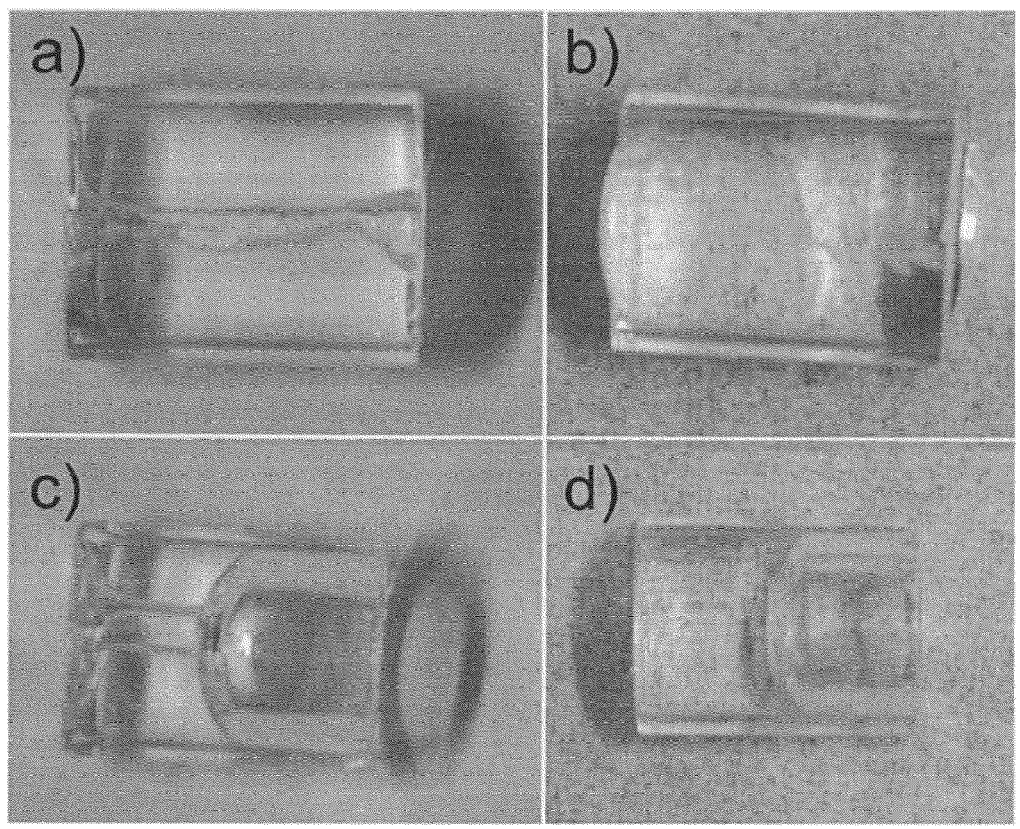
FIG. 11: Two examples of hydrogel-filled tubes with channels created by the application of a laser before (a/c) and after (b/d) swelling them in BSS.
Figure 12:
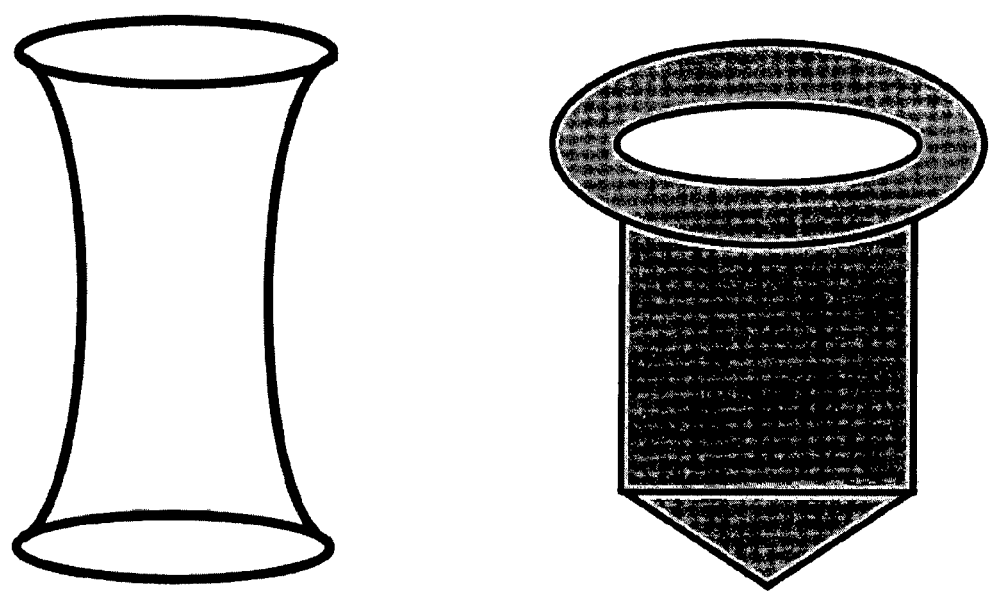
FIG. 12: Schematic presentation of two exemplary shapes of an ocular device according to the invention The following non-limiting examples illustrate the present invention in more detail.

FIG. 11 shows two examples of hydrogel-filled tubes (L=10 mm; ID=5 mm; Mn(HA)=100 kDa; β(HA)=15 mg/mL; TG=0.57; gels synthesized in TRIS/BSS (BSS: balanced saline solution buffer) (c(TRIS)=0.4 mol/l; pH=8.5)) with channels created by the application of a laser before (a/c) and after (b/d) swelling them in BSS. The channels were burned through hydrogels with 0.5 mm (a) and 1 mm (c) width. In both cases the channels were not seen visually after swelling for 48 h in BSS (b/d) (crosslinker: MBAA; N,N'-Methylenebis(acrylamide)).

The gel fabrication with HA, immobilization via epoxy groups and crosslinking was the same as described before (e.g. in Example 1 above) except for the above mentioned glass fiber or the laser.

The preliminary experiments with the "defect" have been conducted with glass, since it has the same surface chemistry as titanium but it is easier to handle and the gel can be visualized if a fluorescently labeled HA is used.

The invention claimed is:

1. An ocular device for regulating intraocular fluid pressure comprising a tubular body wherein the tubular body comprises: (a) titanium; (b) a silanized inner surface; and (c) thiol-modified hyaluronic acid molecules immobilized on the silanized inner surface via covalent bonds resulting from a coupling reaction between epoxide groups on the silanized inner surface and hydroxyl- and/or thiol groups of the thiol-modified hyaluronic acid molecules, wherein the silanized inner surface having thiol-modified hyaluronic acid molecules immobilized thereon comprises some or all of an inner surface of the tubular body.

2. The ocular device according to claim 1, wherein the tubular body further comprises: (d) a silanized outer surface; and (e) thiol-modified hyaluronic acid molecules immobilized on the silanized outer surface via covalent bonds resulting from a coupling reaction between epoxide groups on the silanized outer surface and hydroxyl- and/or thiol groups of the thiol-modified hyaluronic acid molecules, wherein the silanized outer surface having thiol-modified hyaluronic acid molecules immobilized thereon comprises some or all of an outer surface of the tubular body.

3. The ocular device according to claim 1, wherein the silanized inner surface having thiol-modified hyaluronic acid molecules immobilized thereon comprises all of the inner surface of the tubular body.

4. The ocular device according to claim 1, wherein the tubular body has a length in a range from 2.5 mm to 0.3 mm, and a diameter in a range from 2 mm to 100 μm, and a lumen with an inner diameter in a range from 1 mm to 50 μm.

5. The ocular device according to claim 1, wherein the tubular body and/or a lumen thereof has an annular cross-section.

6. The ocular device according to claim 1, wherein the thiol-modified hyaluronic acid molecules immobilized on the silanized inner surface of the tubular body are linked with further hyaluronic acid molecules to form a hyaluronic acid hydrogel.

7. The ocular device according to claim 6, wherein the thiol-modified hyaluronic acid molecules immobilized on the silanized inner surface are linked with the further hyaluronic acid molecules to form the hyaluronic acid hydrogel via crosslinkers with acrylic groups selected from the group consisting of polyethylene(glycol)-diacrylamide (PEG-DA), N,N'-methylenebisacrylamide (MBBA),$N^3,N^5$-bis(2-acrylamidoethyl)pyridine-3,5-dicarboxamide,3,5-((2-acrylamidoethyl)carbamoyl)-1-methylpyridin-1-ium iodide, piperazine diacrylamide, N,N'-(1,2-dihydroxyethylene)-bisacrylamide, and N,N-bis(acryloyl) cystamine.

8. The ocular device according to claim 6, wherein at least one of the thiol-modified hyaluronic acid molecules immobilized on the silanized inner surface and the hyaluronic acid hydrogel is/are linked with additional cell adhesion-regulating molecules.

9. The ocular device according to claim 1, wherein the tubular body is free from cell adhesion-regulating molecules other than hyaluronic acid.

10. The ocular device according to claim 1, which is a stent free from mechanical valves or other mechanical means for actively regulating a flow of intraocular fluid through said device.

11. The ocular device according to claim 1, wherein a lumen of the tubular body is filled with a compressible crosslinked hyaluronic acid hydrogel which comprises a channel extending in a longitudinal direction of the tubular body, which channel is closed as long as an external liquid pressure applied to an end portion of the tubular body is below a specific threshold value, and which channel is open if said external liquid pressure is above said threshold value and compresses the hyaluronic acid hydrogel.

12. The ocular device according to claim 11, wherein structural properties of the crosslinked hyaluronic acid hydrogel are provided in predetermined ranges by adjusting one or more of parameters selected from the group consisting of hyaluronic acid concentration, thiolation degree of hyaluronic acid, type of crosslinker(s) and concentration of crosslinker(s).

13. A method for preparing the ocular device according to claim 1 comprising at least the following steps:
 a) providing the tubular body having predetermined dimensions;
 b) silanizing the inner surface of the tubular body or an outer surface and the inner surface of the tubular body to provide the epoxide groups thereon;
 c) reacting the epoxide groups with the hydroxyl and/or thiol groups of the thiol-modified hyaluronic acid molecules to covalently immobilize the thiol-modified hyaluronic acid molecules to provide immobilized hyaluronic acid molecules on the inner surface or on the inner surface and the outer surface; and d) optionally crosslinking of the immobilized hyaluronic acid molecules with further hyaluronic acid molecules and suitable crosslinkers to form a hyaluronic acid hydrogel.

14. A method for preparing an ocular device according to claim 11, comprising at least the following steps:
   a) providing the tubular body having predetermined dimensions and providing an elongated removable element, in the lumen of the tubular body in a predetermined distance from inner surfaces of the tubular body, and which element extends in the longitudinal direction of the lumen of the tubular body;
   b) silanizing the inner surface of the tubular body or an outer surface and the inner surface of the tubular body to provide the epoxide groups thereon;
   c) reacting the epoxide groups with the hydroxyl and/or thiol groups of the thiol-modified hyaluronic acid molecules to provide immobilized hyaluronic acid molecules on the inner surface or on the inner surface and the outer surface;
   d) crosslinking the immobilized hyaluronic acid molecules on at least the inner surface with further hyaluronic acid molecules and suitable crosslinkers to form a crosslinked hyaluronic acid hydrogel; and
   e) removing the elongated removable element after gel formation leaving a channel with dimensions corresponding to that of said elongated element in the crosslinked hyaluronic acid hydrogel.

15. A method for preparing the ocular device according to claim 11 comprising at least the following steps:
   a) providing the tubular body having predetermined dimensions;
   b) silanizing the inner surface of the tubular body or an outer surface and the inner surface of the tubular body to provide the epoxide groups thereon;
   c) reacting the epoxide groups with the hydroxyl and/or thiol groups of the thiol-modified hyaluronic acid molecules to provide immobilized hyaluronic acid molecules on the inner surface or on the inner surface and the outer surface;
   d) crosslinking the immobilized hyaluronic acid molecules on at least the inner surface with further hyaluronic acid molecules and suitable crosslinkers to form a crosslinked hyaluronic acid hydrogel which fills the lumen of the tubular body; and
   e) generating a channel in the crosslinked hyaluronic acid hydrogel which extends in the longitudinal direction of the tubular body by irradiating an open end portion of the crosslinked hyaluronic acid hydrogel obtained after step d) above in the lumen of the tubular body with a laser beam in the longitudinal direction of the tubular body and the crosslinked hyaluronic acid hydrogel with a sufficient energy and for a sufficient time period to obtain an end-to-end channel in said crosslinked hyaluronic acid hydrogel.

* * * * *